US012408995B2

United States Patent
Chatzizisis et al.

(10) Patent No.: US 12,408,995 B2
(45) Date of Patent: Sep. 9, 2025

(54) ARTIFICIAL INTELLIGENCE-BASED REAL-TIME PLANNING AND OPTIMIZATION OF PERCUTANEOUS CORONARY INTERVENTIONS

(71) Applicant: ComKardia, Inc., Newton, MA (US)

(72) Inventors: Ioannis S. Chatzizisis, Sunny Isles, FL (US); Evangelia I. Zacharaki, Patras (GR); Kaiming Li, Riverside, CA (US); Praveen Ravichandran, Ottawa (CA)

(73) Assignee: ComKardia, Inc., Newton, MA (US)

( * ) Notice: Subject to any disclaimer, the term of this patent is extended or adjusted under 35 U.S.C. 154(b) by 0 days.

(21) Appl. No.: 18/736,285

(22) Filed: Jun. 6, 2024

(65) Prior Publication Data

US 2024/0407854 A1    Dec. 12, 2024

Related U.S. Application Data

(60) Provisional application No. 63/506,414, filed on Jun. 6, 2023.

(51) Int. Cl.
*A61B 34/20* (2016.01)
*A61B 5/00* (2006.01)
(Continued)

(52) U.S. Cl.
CPC ............ *A61B 34/20* (2016.02); *A61B 5/0215* (2013.01); *A61B 5/4842* (2013.01); *A61B 34/10* (2016.02);
(Continued)

(58) Field of Classification Search
CPC ..... A61B 34/20; A61B 5/0215; A61B 5/4842; A61B 34/10; A61B 2034/104;
(Continued)

(56) References Cited

U.S. PATENT DOCUMENTS

2006/0036167 A1    2/2006 Shina
2013/0329030 A1*   12/2013 Tolkowsky .......... A61B 5/0044
                                                           348/77
(Continued)

FOREIGN PATENT DOCUMENTS

WO    WO-2024186355 A1 *    9/2024    ............. A61B 90/37

OTHER PUBLICATIONS

Li et al (Automatic coronary artery segmentation and diagnosis of stenosis by deep learning based on computed tomographic coronary angiography, Cardiac vol. 32, pp. 6037-6045 Published: Apr. 8, 2022.*

(Continued)

*Primary Examiner* — Serkan Akar
(74) *Attorney, Agent, or Firm* — Foley Hoag LLP; Erik A. Huestis; Joshua S. Matloff

(57) ABSTRACT

Systems and methods disclosed herein provide a method for real-time PCI guidance. A method comprises receiving one or more images of a blood vessel from an imaging modality system, the blood vessel having a lumen, a lumen surface, and a wall; building a 3D model of the blood vessel based on the one or more images; segmenting one or more materials between the lumen and the wall of the blood vessel; reconstructing the blood vessel based on the one or more images; assigning material properties to the reconstructed surface of the blood vessel; determining a wall thickness, a plaque thickness, a lumen area, a plaque eccentricity and one or more plaque constituents; guiding an interventional procedure in real-time based on the 3D reconstructed vessel lumen surface and segmented materials; and performing balloon pre-dilation, a percutaneous coronary intervention, and balloon post-dilation with the 3D reconstructed vessel lumen surface and segmented materials.

27 Claims, 12 Drawing Sheets

(51) Int. Cl.
  *A61B 5/0215*  (2006.01)
  *A61B 34/10*   (2016.01)
  *G06T 7/11*    (2017.01)

(52) U.S. Cl.
  CPC ........... *G06T 7/11* (2017.01); *A61B 2034/104* (2016.02); *A61B 2034/105* (2016.02); *G06T 2207/20084* (2013.01); *G06T 2207/30104* (2013.01); *G06T 2207/30172* (2013.01)

(58) Field of Classification Search
  CPC ............... A61B 2034/105; G06T 7/11; G06T 2207/20084; G06T 2207/30104; G06T 2207/30172
  See application file for complete search history.

(56) References Cited

U.S. PATENT DOCUMENTS

| | | |
|---|---|---|
| 2021/0259777 A1 | 8/2021 | Chatzizisis |
| 2022/0172368 A1* | 6/2022 | Lavi .......................... G06T 7/70 |
| 2022/0175269 A1 | 6/2022 | Lu et al. |
| 2022/0335612 A1 | 10/2022 | Bruch-El et al. |

OTHER PUBLICATIONS

Li et al (Year: 2022).*
International Search Report and Written Opinion for International Application No. PCT/US24/32833 dated Sep. 26, 2024.

* cited by examiner

ARTIFICIAL INTELLIGENCE-BASED REAL-TIME PLANNING AND OPTIMIZATION OF PERCUTANEOUS CORONARY INTERVENTIONS

RELATED APPLICATION(S)

This application claims the benefit of priority to U.S. Provisional App. No. 63/506,414, filed on Jun. 6, 2023, which is incorporated herein by reference in its entirety.

TECHNICAL FIELD

The invention relates generally to a percutaneous coronary intervention (PCI) guiding system, and, in particular, to systems and methods for an artificial intelligence (AI) based PCI guiding system for coronary interventional procedures.

BACKGROUND

Coronary artery disease is the leading cause of death in the world. Stents are implanted in 70-90% of the 1.3 million percutaneous coronary interventions performed annually in the US.

Current approaches to external artery angiography systems can only show the 2D artery images without a reconstructed clear 3D image. This can occur using both sectional intravascular ultrasound (IVUS), and optical coherence tomography (OCT) images. In the 2D IVUS and OCT images, the identification of lumen and wall borders is cumbersome and images are often not clear by human vision. It is even harder to segment calcium, fibrous and fibro-lipid. Furthermore, the size, shape, position, and volume of the above materials are very difficult to determine by human vision. Based on solid mechanics, the different materials have different responses to PCI. Therefore, the materials must be segmented clearly and reconstructed in 3D to further use a solid mechanics model providing guidance to operators during the procedure.

Although many research projects have been undertaken in the last ten years, the image and data processing still take too long (usually a few hours) and cannot be used in real time in the PCI procedure room with following root causes: too many steps are needed using different software, and too many manual processes are used in 2D image segmentations and 3D reconstructions. Therefore, the PCI planning for assessment of lesion significance, selection of stenting technique and stent size is still based on general rules and lacks personalization.

Embodiments of the present disclosure combine different software processes into one software application and reduce the processing time from a few hours to a few minutes with AI based automated processes.

SUMMARY

According to certain aspects of the present disclosure, systems and methods are disclosed for an AI based PCI guiding system.

In one embodiment, a method comprises receiving one or more images of a blood vessel from an imaging modality system, the blood vessel having a lumen, a lumen surface, and a wall; building a 3D model of the blood vessel based on the one or more images; segmenting one or more materials between the lumen and the wall of the blood vessel; reconstructing the surface of the blood vessel based on the one or more images; assigning material properties to the reconstructed surface of the blood vessel; determining a wall thickness, a plaque thickness, a lumen area, a plaque eccentricity and one or more plaque constituents; guiding an interventional procedure in real-time based on the 3D reconstructed vessel lumen surface and segmented materials; and performing balloon pre-dilation, PCI, and balloon post-dilation with the 3D reconstructed vessel lumen surface and segmented materials.

In another embodiment, a system for guiding a real-time medical procedure comprises an imaging modality system; a computing node comprising a computer readable storage medium having program instructions embodied therewith, the program instructions executable by a processor of the computing node to cause the processor to perform a method comprising: receiving one or more images of a blood vessel from an imaging modality system, the blood vessel having a lumen, a lumen surface, and a wall; building a 3D model of the blood vessel based on the one or more images; segmenting one or more materials between the lumen and the wall of the blood vessel; reconstructing the surface of the blood vessel based on the one or more images; assigning material properties to the reconstructed surface of the blood vessel; determining a wall thickness, a plaque thickness, a lumen area, a plaque eccentricity and one or more plaque constituents; guiding an interventional procedure in real-time based on the 3D reconstructed vessel lumen surface and segmented materials; and performing balloon pre-dilation, PCI, and balloon post-dilation with the 3D reconstructed vessel lumen surface and segmented materials.

In an alternate embodiment, a computer program product for guiding a real-time medical procedure comprises a computer readable storage medium having program instructions embodied therewith, the program instructions executable by a processor to cause the processor to perform a method comprising: receiving one or more images of a blood vessel from an imaging modality system, the blood vessel having a lumen, a lumen surface, and a wall; building a 3D model of the blood vessel based on the one or more images; segmenting one or more materials between the lumen and the wall of the blood vessel; reconstructing the surface of the blood vessel based on the one or more images; assigning material properties to the reconstructed surface of the blood vessel; determining a wall thickness, a plaque thickness, a lumen area, a plaque eccentricity and one or more plaque constituents; guiding an interventional procedure in real-time based on the 3D reconstructed vessel lumen surface and segmented materials; and performing balloon pre-dilation, PCI, and balloon post-dilation with the 3D reconstructed vessel lumen surface and segmented materials.

BRIEF DESCRIPTION OF THE DRAWINGS

The accompanying drawings, which are incorporated into and constitute a part of this specification, illustrate various exemplary embodiments and together with the description, serve to explain the principles of the disclosed embodiments.

DETAILED DESCRIPTION

Figure 1:
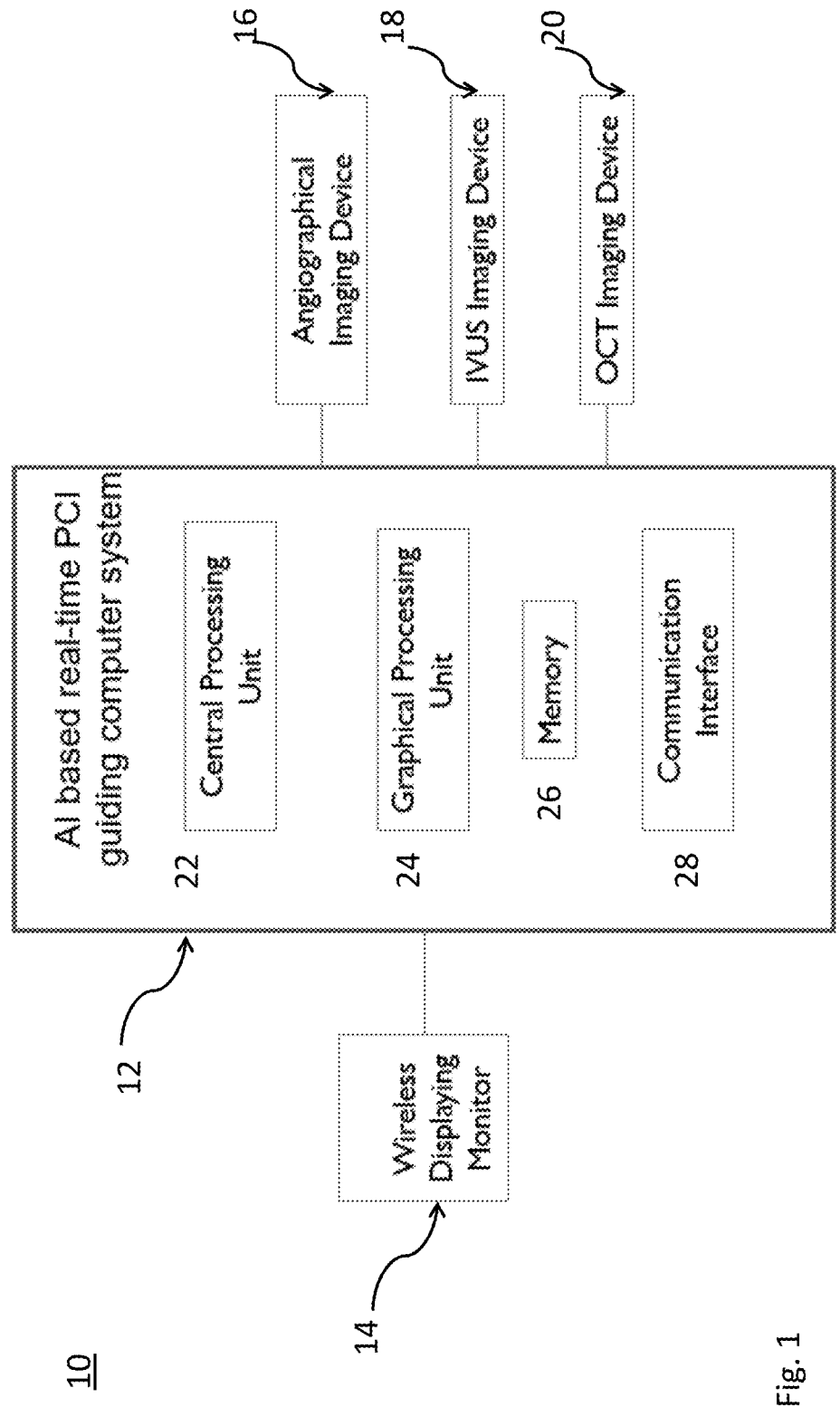
FIG. 1 is a block diagram illustrating a system for interventional procedures, in accordance with one or more embodiments of this disclosure.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

The present disclosure is directed to an AI-based PCI guiding method with 3D imaging and solid and fluid mechanics for real-time personalized interventional procedures. A PCI guidance is disclosed with reference to FIGS. 1 through 10. The AI-based PCI guiding method can be used to guide percutaneous interventions in the procedure lab. The 3D models can be used in a 3D environment and in a time-effective fashion to guide the events occurring during the PCI procedure. AI-based PCI can characterize the local biomechanical microenvironment pre- and post-PCI, providing a method for PCI optimization that can be used clinically.

While several studies on AI-based PCI guidance have been undertaken, these studies are only available in limited situations. This disclosure presents a new method for real-time PCI guidance.

Embodiments of the present disclosure include an AI-based 3D modeling method with a 3D reconstruction algorithm from the 2D vessel lumen and a surface of the vessel lumen based on invasive or non-invasive images provided to the system. A deep learning-based image segmentation method segments the lumen, vessel wall, calcium, fibrous, fibrous lipid, and other materials included in the blood vessel. The method combines an AI-based 3D imaging system with solid mechanics and fluid mechanics for real-time PCI procedures, including balloon pre-dilation, PCI, and balloon post-dilation, as well as for assessing stent and vessel morphometric and biomechanical measures to guide operators for PCI procedures.

In some embodiments, the 2D vessel lumen detection includes the lumen centerlines, boundaries, and stenosis region detection.

In some embodiments, the computer-implemented method further includes 3D artery reconstruction from multiple viewed 2D images.

In some embodiments, the AI-based image segmentation methods include sample preparing, labeling, modeling, training, segmenting of materials and/or lumens and walls, etc.

In some embodiments, the computer-implemented method further includes generating a computational model of a stent and balloon based on the 3D reconstruction results.

In some embodiments, the method includes guiding and positioning the modeled stent and balloon within the 3D reconstructed vessel lumen.

In some embodiments, the balloon pre-dilation, PCI, and balloon post-dilation simulations are computationally produced using solid mechanics.

FIG. 1 illustrates a system for the AI-based PCI guiding method, in accordance with one or more embodiments of this disclosure. The system 10 includes a computer system 12 (e.g., an AI-based computer program and other software for the imaging devices). Computer system 12 is only one example of a suitable computing system and is not intended to suggest any limitation as to the scope of use or functionality of embodiments described herein. Regardless, computer system 12 is capable of being implemented and/or performing any of the functionality set forth hereinabove. Computer system 12 is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 12 may be described in the general context of computer system-executable instructions, such as program modules, being executed by a computer system. Generally, program modules may include routines, programs, objects, components, logic, data structures, and so on that perform particular tasks or implement particular abstract data types. Computer system 12 may be practiced in distributed cloud computing environments where tasks are performed by remote processing devices that are linked through a communications network.

The system 10 further includes two or more medical imaging devices, such as an angiographical imaging device 16, an IVUS imaging device 18, an OCT imaging device 20, or non-invasive coronary CT angiography for example, which are communicatively coupled to the AI-based computer systems. The one or more medical imaging devices may be physically connected (e.g., wired) to the AI-based computer system, wirelessly connected (e.g., via Wi-Fi, WLAN, Bluetooth, or the like), and/or communicatively coupled by at least one portable storage device (e.g., USB drive, portable hard drive, or the like) that is configured to store data collected by the medical imaging devices so that the data can be transferred to the AI-based computer system.

Examples of an invasive or non-invasive medical imaging device include, but are not limited to, a CT scanner, an X-ray scanner, a fluoroscope, an ultrasound scanner. In embodiments, the one or more invasive or non-invasive medical imaging devices may include any number or combination of the aforementioned devices.

The AI-based computer systems may be configured to implement the computational platform by performing various functions, steps and/or operations discussed herein. In embodiments, a computer system 12 (or each computer system of a cluster) includes one or more Central Processing Unit (CPU) processors 22 and Graphical Processing Unit (GPU) processors 24, a memory 26, and a communication interface 28.

CPU 22 provides processing functionality for at least the computer system 12 and can include any number of processors, microprocessors, microcontrollers, circuitry, field programmable gate array (FPGA) or other processing systems and resident or external memory for storing data, executable code and other information accessed or generated by the computer system. It is contemplated that a GPU may also be utilized. CPU 22 can execute one or more software programs embodied in a non-transitory computer readable medium (e.g., memory 26) that implements techniques/operations described herein.

Memory 26 can be an example of tangible, computer-readable storage medium that provides storage functionality to store various data and/or program code associated with operation of the computer system 12/CPU 22, such as software programs and/or code segments, or other data to instruct the processor, and possibly other components of the computer system, to perform the functionality described herein. Thus, memory 26 can store data, such as a program of instructions for operating the computer system, including its components (e.g., processor, communication interface, etc.), and so forth. It should be noted that while a single memory is described, a wide variety of types and combinations of memory (e.g., tangible, non-transitory memory) can be employed. Memory 26 can be integrated with the CPU 22, can comprise stand-alone memory, or can be a combination of both.

The communication interface 28 can be operatively configured to communicate with components of the computer system. For example, communication interface 28 can be configured to retrieve data from the CPU 22 or other devices (e.g., medical imaging devices, other computer systems, local/remote servers, etc.), transmit data for storage in the memory, retrieve data from storage in memory 26, and so forth.

The communication interface 28 can also be communicatively coupled with the CPU 22 to facilitate data transfer between components of the computer system 12 and the CPU 22. It should be noted that while the communication interface 28 is described as a component of the computer system 12, one or more components of the communication interface 28 can be implemented as external components communicatively coupled to the computer system 12 via a wired and/or wireless connection. The computer system 12 can also include and/or connect to a speaker input/output (I/O) devices (e.g., via the communication interface 28), such as an input device (e.g., a mouse, a trackball, a trackpad, a joystick, a touchpad, a touchscreen, a keyboard, a keypad, a microphone (e.g., for voice commands), etc.) and/or an output device (e.g., a display, such as Wireless Displaying Monitor 14, a speaker, a tactile feedback device, etc.). In embodiments, communication interface 28 may also include or may be coupled with a transmitter, receiver, transceiver, physical connection interface, or any combination thereof.

It shall be understood that any of the functions, steps or operations described here are not necessarily all performed by one computer system. In some embodiments, various functions, steps, or operations may be performed by one or more computer systems. For example, one or more operations and/or sub-operations may be performed by a first computer system, additional operations and/or sub-operations may be performed by a second computer system, and so forth. Furthermore, some of the operations and/or sub-operations may be performed in parallel and not necessarily in the order that they are disclosed herein.

The present disclosure may be embodied as a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Python, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Figure 2A:
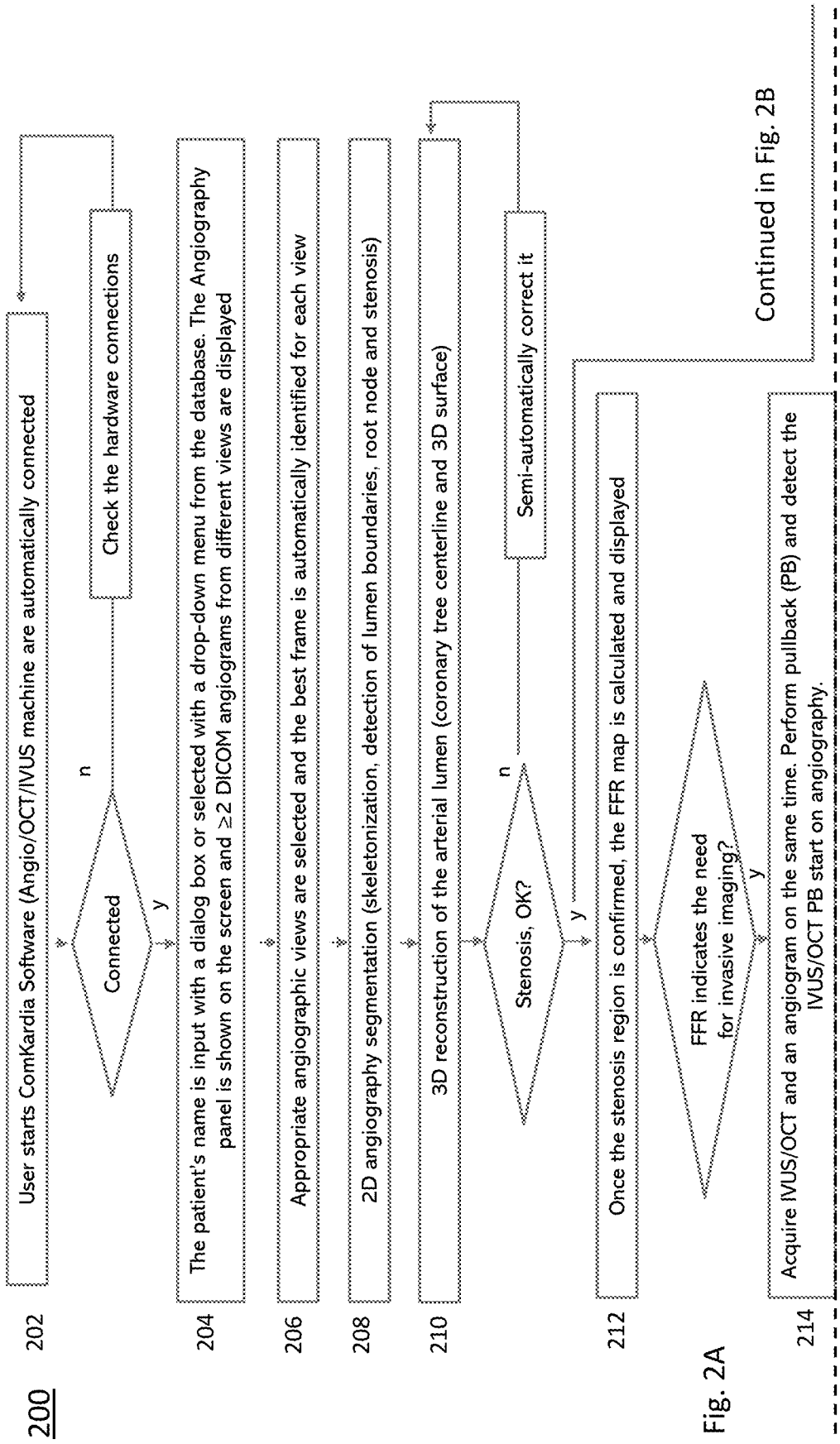
FIGS. 2A-B is a flow diagram illustrating a procedure, in accordance with one or more embodiments of this disclosure.
Figure 2B:
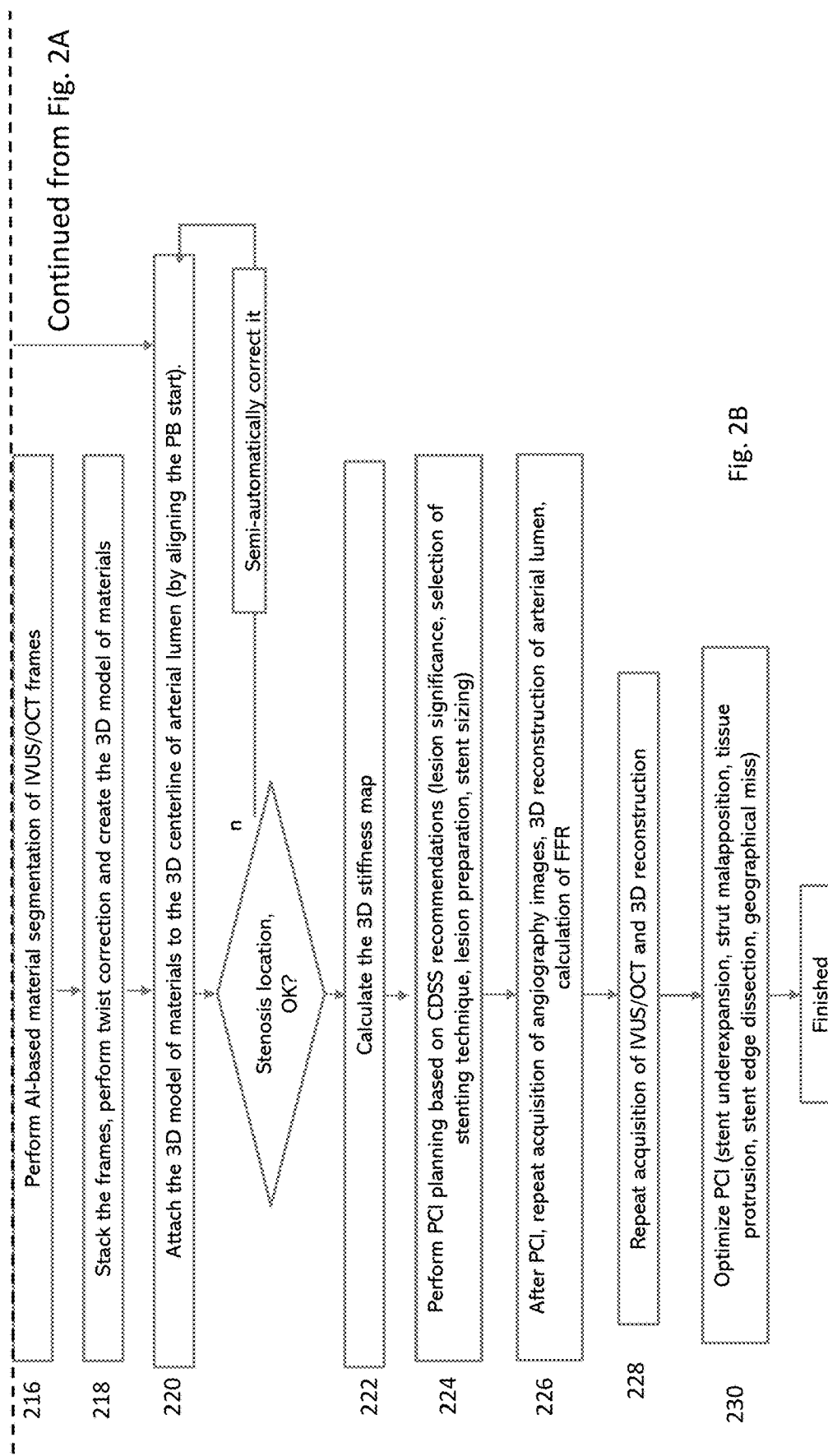

FIGS. 2A-2B is a flow diagram illustrating an exemplary AI-based PCI guiding method 200. In embodiments, the method 200 is utilized by a processor and includes the following steps (e.g., steps 202-230).

In step 202, the medical imaging devices (such as angiography, OCT, and IVUS devices) are automatically connected to the AI-based computer. When the user starts a software, this automatic connection can be shown, for example, as an icon on the screen or as a pop-up message. The system can run a check to ensure connection; if the connection query comes back as "no," the user may check hardware connections and/or restart the software until a connection query returns as "yes."

Once the software is started in step 204, the patient's name is input with a dialog box or selected with a drop-down menu from the database. The Angiography panel is shown on the screen and at least 2 DICOM angiograms from different views are displayed. The invasive or non-invasive imaging data from a certain patient is collected for one or more vessels (e.g., a coronary artery bifurcation or any other vasculature or portion thereof). For example, if the imaging modality using the software is an angiographic device, the angiographic panel is shown on a display screen with the DICOM image(s) and at least two image views.

Appropriate angiographic views are selected and the best frame is automatically identified for each view at step 206.

The AI-based computer program can be configured to generate a 3D reconstruction of a bifurcation lumen and wall/plaque based on an invasive (e.g., angiography) or non-invasive (computed tomography angiography or magnetic resonance angiography) imaging modality or any combination of these modalities. Special emphasis is put on reconstructing the true dimensions (thickness, eccentricity) of the arterial wall and plaque. Furthermore, the 3D reconstructed bifurcation is patient specific. The AI-based computer may be configured to generate the 3D reconstruction of at least one vessel lumen and a surface of the vessel lumen (e.g., the lumen wall and/or any plaque built up on the lumen wall) based on the invasive or non-invasive imaging data collected by the one or more imaging devices using any of the tools and/or techniques described in the example embodiments discussed below.

In some embodiments, a computerized framework is provided to automatically produce a volumetric model of the surface of the vessel lumen from digital X-ray angiographic images in two or more projections (views). The framework includes three main components. First the best frame is automatically identified in each of the projected views, such that the vessel lumen is in the end-diastolic cardiac phase and has good image contrast. The angiographic frames, selected as best for each view, are then introduced in a computerized methodology that uses AI to automatically extract the coronary artery tree in the 2D projection image and also to recognize (and label) individual branches. Once the different projection images are segmented, an image analysis algorithm is applied that allows to detect corresponding points (landmark pairs) between the different angiographic views. Those landmark pairs are used to resolve the transformation between the different views and also the mapping from the object space to the individual 2D projection images, which then leads to the construction of a 3D geometric model of the vessel lumen from angiographic images.

A component comprises recognition of the best image frame, corresponding to the end-diastolic phase and having high image contrast. For training, the artificial neural network takes as input the sequential frames of X-ray angiography and extracts an attention map by detecting areas of significant motion. A temporal signal trajectory is formed by averaging the signal intensity within the attention map for each frame. Peaks with specific characteristics in this signal trajectory are detected and used as candidate frames in the end-diastolic phase. A confidence score is formulated based on the peak properties to rank those candidate frames. Rare cases, for which less than three candidate frames are detected, are handled through an alternative computerized approach that performs temporal frequency analysis. Specifically, image enhancement is performed by removing low and high frequencies, such as by applying a Fast Fourier Transform (FFT) on each frame, followed by bandpass filtering and reconstruction by inverse FFT. Each filtered frame is then averaged across spatial dimensions and the obtained intensity values for all frames are concatenated into a vector forming a temporal trajectory. The candidate end-diastolic frames are detected by temporal pattern analysis of this signal trajectory. The identified candidate frames are also ranked according to the contrast flow and noise level in the angiographic image. The image contrast is quantitatively assessed by evaluating the response of a ridge filter on the attention map. A composite score is calculated taking into account the confidence ranking of end-diastole recognition and image contrast ranking. The frame with the highest composite score is finally used as the best frame for the subsequent segmentation and reconstruction of coronary arteries. The best frames from each projection image are then segmented. The segmented image is used to extract the coronary vessel tree in the form of a skeletal graph.

Figure 8:
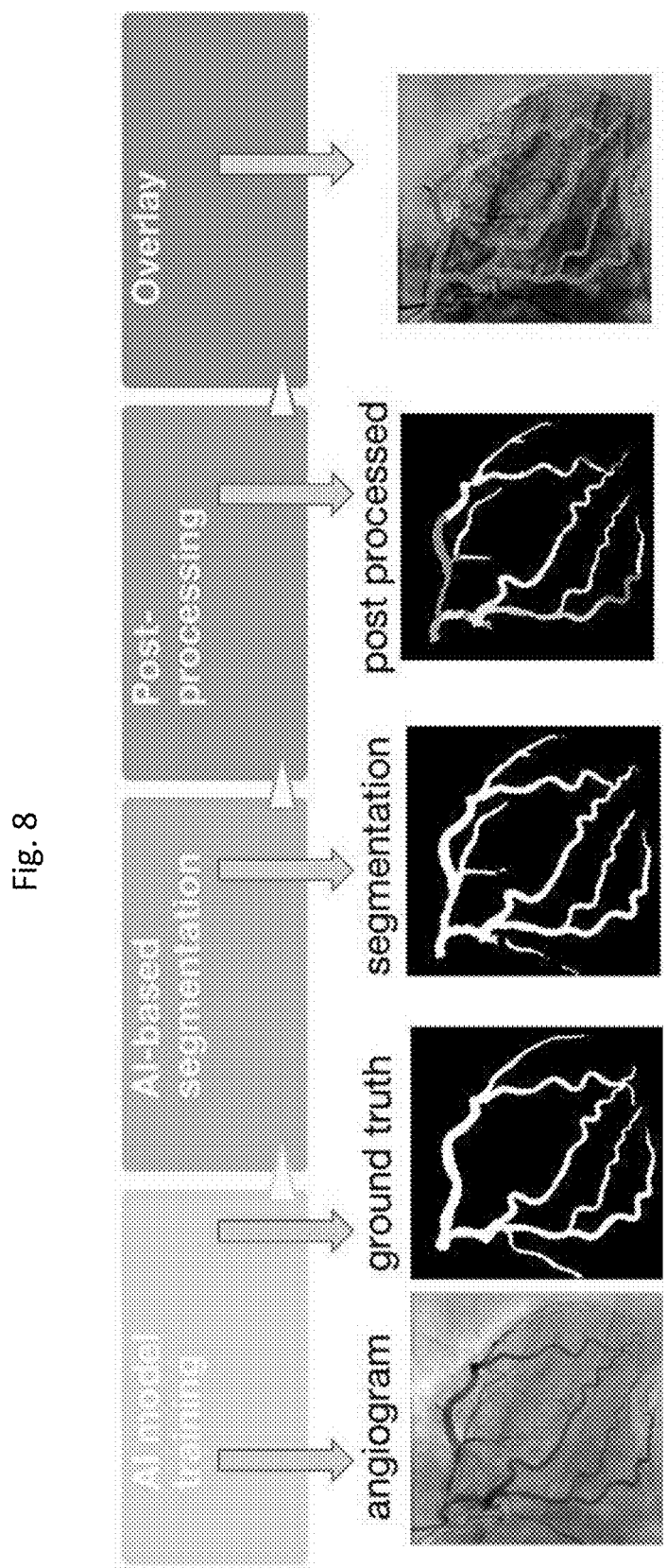
FIG. 8 illustrates automatic vessel lumen segmentation, in accordance with one or more embodiments of the present disclosure.

Another component comprises vessel lumen segmentation and branch labelling of the coronary tree. The previously trained artificial neural network automatically differentiates between left and right coronary arteries (LCA/RCA) in digital angiographic images. After identifying the artery, an artery-specific lightweight deep neural network is used to segment the vessel lumen in the best frame of each angiographic projection image. A third neural network is used to segment and also classify the individual branches. The binary and multi-class segmentation outputs are aggregated and further improved using image processing and connectivity analysis to produce the final vessel lumen segmentation and branch labeling. An example of automatic vessel lumen segmentation is shown in FIG. 8.

Once the coronary trees are generated, the system matches the trees between different projections, i.e. to identify corresponding points (pairs of landmarks) that can be used to perform 3D reconstruction. This involves the following components: (i) skeletonization of binary segmentation, (ii) extraction of a directed graph from the skeleton, (iii) resolving the vessel overlap problem and thereby expressing the coronary tree as a directed acyclic graph, (iv) pruning the trees for each view (through removal of nodes) and/or extending the trees (through addition of nodes) so that the trees across views have similar topology, (v) perform tree matching.

More analytically, the method for finding pairs of landmarks solves an assignment (matching) problem using graph theory and linear programming. To solve the matching problem, a cost function is formulated that assesses topological similarities between the different coronary trees, and also penalizes mismatches that violate the epipolar consistency. The topology is assessed in respect to the root of the coronary tree, which is defined as the ostial coronary artery. In order for the method to be completely automated, the root node of the graph is detected utilizing the multi-class segmentation scores and expert-defined rules. The root node is a significant landmark point and also provides information on the direction of the flow.

Figure 6:
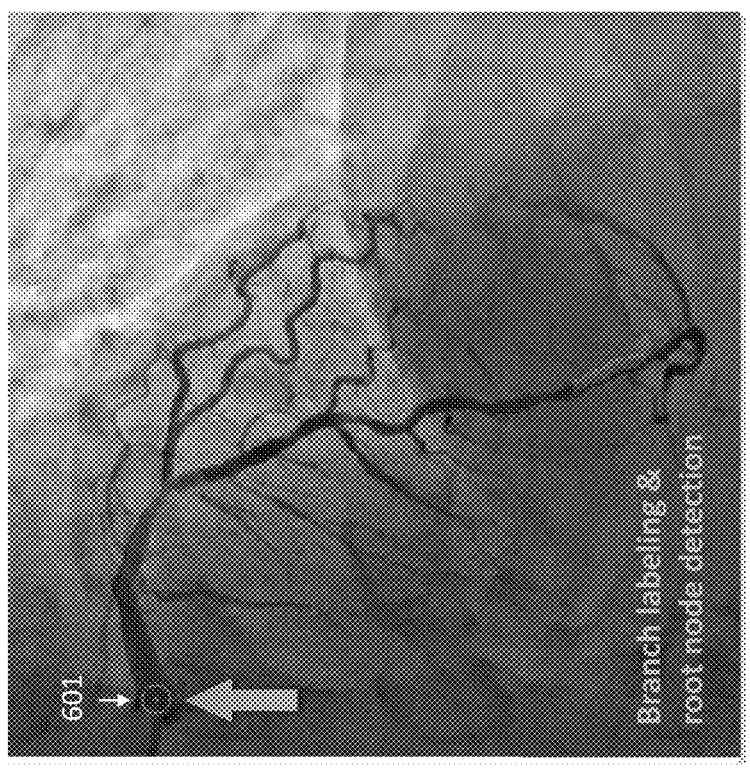
FIG. 6 illustrates an exemplary angiogram segmentation with branch labelling and root node detection image, in accordance with one or more embodiments of this disclosure.

FIG. 6 illustrates an exemplary angiogram segmentation with branch labelling and root node detection (root node 601 further indicated by the circle and arrow). Information from the labeled coronary branches may also be utilized to improve the detection of the corresponding points.

Figure 7:
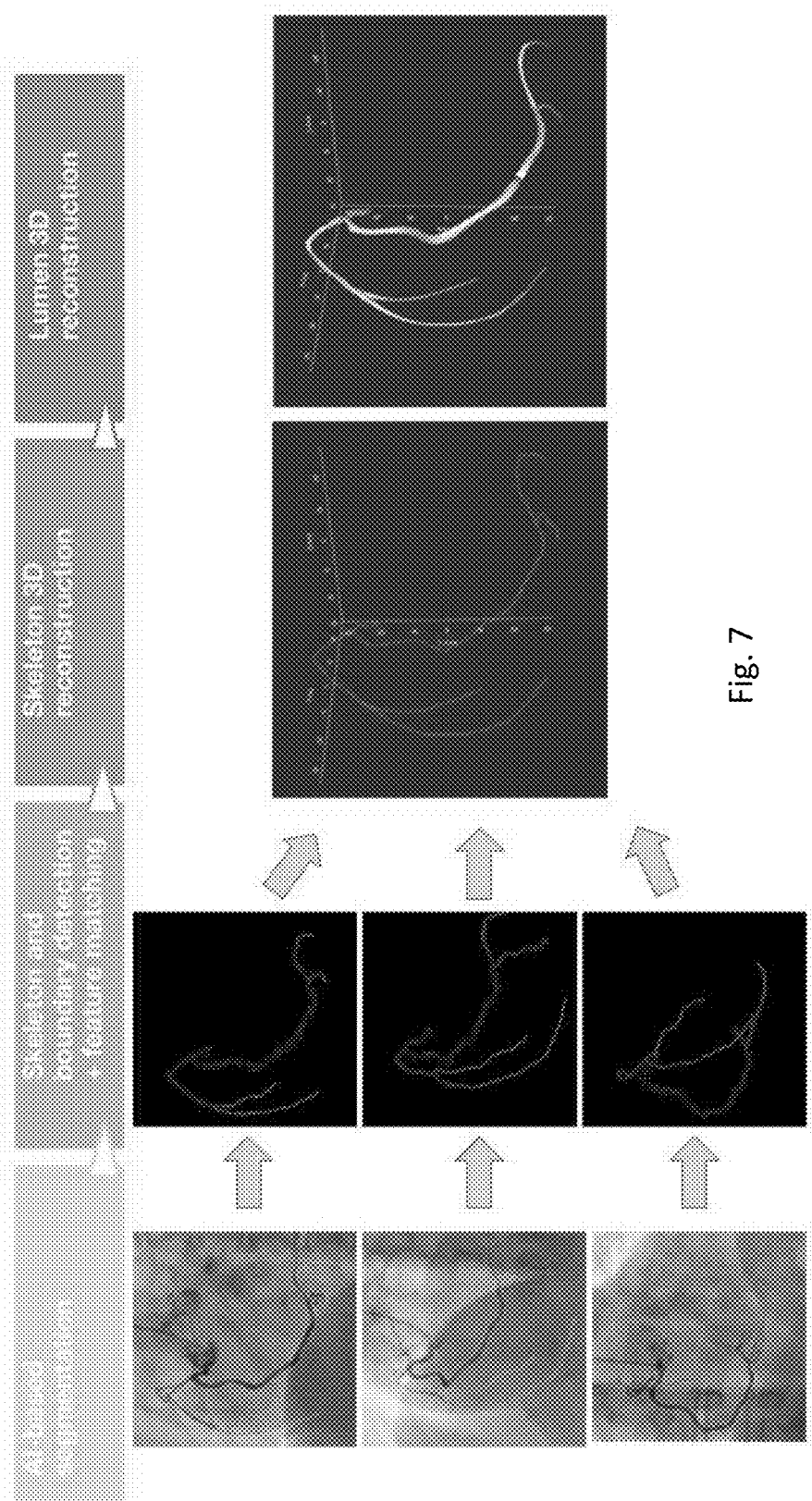
FIG. 7 is an exemplary 3D reconstruction of a lumen from multiple angiographic projection images, in accordance with one or more embodiments of the present disclosure.

In a third component, the 3D reconstruction algorithm completes the reconstruction of the 3D model. A perspective projection model is utilized to describe the visualization of 3D objects into 2D image planes in X-ray angiographic systems. A mathematical function using the perspective projection model and a linear transformation to express the change of coordinate systems across different views further defines the model. The formulated mathematical expression uses a set of optimized parameters based on the anatomic location of corresponding landmark points across the different projection images. First the coronary skeletal tree is reconstructed in 3D by estimating the parameters of a linear motion model subject to the epipolar constraints. The linear transformation allows to correct for rotation, translation and scaling errors, addressing potential movements of the patient during acquisition. Then the derived solution can be utilized as initial estimate in a nonlinear optimization method in order to resolve differences due to non-linear motion. After calculating the position of each node of the skeletal tree in the 3D world coordinate system, the surface of the lumen is reconstructed by detecting the vessel boundary points in each projection image and assuming an elliptical cross-sectional shape. This is illustrated in FIG. 7, an exemplary 3D reconstruction of the lumen from multiple angiographic projection images.

In step 206, appropriate angiographic views are selected and the best frame is automatically identified for each view.

In step 208, 2D angiography segmentation (skeletonization, detection of lumen boundaries, root node and stenosis) occurs automatically.

In step 210, the program automatically reconstructs a 3D model of the arterial lumen with a detected 3D coronary tree centerline and 3D surface. The other stenosis region candidates are also automatically detected as references for the user. A check is run to determine that the stenosis has been accurately detected. If the user indicates that the stenosis detection is incorrect, the user can manually correct this by indicating where the stenosis is located.

The boundary of the blood vessels is extracted by image processing and a mesh of the 3D reconstructed vessel lumen and surface of the vessel lumen is generated. After that, the stenosis regions of the blood vessel are detected on the reconstructed 3D image. In some embodiments of the method, the 3D reconstructed vessel lumen and surface of the vessel lumen are not meshed. In this regard, the 3D reconstructions themselves may be used to perform balloon pre-dilation, stenting and balloon post-dilation computational procedures.

In step 212, a fractional flow reserve map is calculated and displayed after the stenosis region is detected. The fractional flow reserve FFR formula is used to obtain the FFR map. The FFR is determined by measuring the mean aortic pressure and the mean pressure distal to the stenosis during hyperemia, and dividing the mean distal pressure by the mean aortic pressure. The FFR map displays the FFR along the blood vessels and is used to determine risk for each possible surgery location along.

If FFR indicates severe stenosis that need therapy, further assessment is performed through invasive imaging. Step 214 includes acquiring IVUS/OCT and an angiogram on the same time. A pullback (PB) is performed, and detects the IVUS/OCT PB start on angiography. Before starting the IVUS pullback, an angiogram with the IVUS/OCT catheter is acquired and the radiopaque IVUS head (that is visible on the angiogram) is used as landmark to calculate the mapping between the model of materials obtained from invasive imaging and the angiography-derived model of lumen. Automatic pullback is completed, with automatic marking of the IVUS/OCT pullback start on the angiogram.

Once IVUS/OCT images are acquired, in step 216, an AI-based algorithm automatically performs material segmentations (lumen, wall, calcium, fibrous, fibro-lipid) on the IVUS/OCT images using a neural network architecture, for example a U-NET architecture. The U-NET model comprises convolutional layers and two networks, but it is contemplated that any other suitable network architecture can be used. The left side of the U-NET is the down-sampling side with an encoder mechanism for feature extraction. The right side of the U-NET is the up-sampling side with decoder mechanism for generating the output image to the same size as the input image.

In step 218, the program converts the IVUS/OCT sequence of 2D frames into a coherent 3D structure. This is performed automatically by a twist correction algorithm, where the IVUS or OCT frames are rotated around the center-point of the lumen (which is automatically detected in IVUS/OCT) so that the tissues/materials change smoothly in the direction the centerline. Upon alignment of the IVUS/OCT frames, the segmented materials are concatenated into a 3D structure and a mesh is produced for surface reconstruction. The twist correction leads to a smoother surface of the materials.

In step 220, the attaching of the 3D model of materials to the 3D centerline of arterial lumen occurs by aligning the PB start. A mapping between IVUS/OCT and angiography space is calculated and the segmented materials are automatically attached to the 3D centerline of the arterial lumen obtained from angiography. Once attachment occurs, the 3D model of the arterial lumen is integrated with the segmented materials surrounding it and visualized with transparency.

Additionally in step 220, a quality check is run to ensure that the stenosis is ok on the integrated model lumen with surrounding materials, and if needed, a correction is made by fine-tuning the registration.

At step 222, a stiffness map is calculated. This may include broad coverage of materials from lipid to fibrous and calcified, including a wide range of combinations between these materials. In some embodiments, the computer is configured to assign material properties to the 3D reconstructed surface of the vessel lumen by determining wall or plaque thickness, lumen area, plaque eccentricity and plaque constituents based on invasive or non-invasive imaging. In some embodiments, the computer is further configured to assign material properties to the 3D reconstructed surface of the vessel lumen by dividing the vessel lumen into sequential zones of plaque material and assigning a value (e.g., a quarter number or any other incremental value) ranging from purely calcium plaque material to purely lipid plaque material. In some embodiments, the computer is configured to assign plaque plasticity based on the material properties assigned to the 3D reconstructed plaque. Additionally, the computer is configured to assign material properties to the 3D reconstructed surface of the vessel lumen based on invasive or non-invasive imaging data collected by the one or more imaging devices using any of the tools and/or techniques described in the example embodiments.

After assigning realistic material properties to the arterial wall and plaque based on the segmented imaging data received from one or more medical imaging devices, in step 224, an automatic decision support system (CDSS) is implemented for PCI planning. Lumen and plaque morphometry are utilized to make decisions about a lesion preparation technique, PCI sizing and positioning (stent, drug-coated balloon, etc.), and bifurcation decisions about PCI technique.

Additionally, in step 224, a recommendation of pre-dilatation technique based on plaque stiffness is made. The proposed stent length and diameter are superimposed on the displayed angiogram. For bifurcation, a stent technique is proposed based on bifurcation angle and disease complexity. The material properties are assigned to the 3D reconstructed blood vessels. For example, the computer is configured to assign material properties to the 3D reconstructed surface of the vessel lumen based on the invasive or non-invasive imaging data collected by one or more imaging devices.

In step 226, after the PCI is performed, acquisition of angiography images, 3D reconstruction of arterial lumen, and calculation of FFR is repeated. The acquisition of the IVUS/OCT and 3D reconstruction is repeated in step 228. In step 230, the PCI is optimized, including stent underexpansion, strut malapposition, tissue protrusion, stent edge dissection, and/or geographical miss). At this point, the process may be considered finished.

In some embodiments, CDSS recommendations are optimized. The material properties of stents and balloons are imported by the program and used to generate a model of a stent and balloon. The true stent design and materials, as well as realistic pre- and post-dilation balloon geometries with compliant, semi-compliant and non-compliant properties are incorporated in the computational platform. For example, the computer can be configured to import design and material properties of the stents and balloons based on invasive or non-invasive imaging data received from one or more medical imaging devices. Alternatively, or additionally, the computer can be configured to import design and material properties of the stents and balloons from one or more databases including manufacturer-provided data. The computer can be configured to generate a model of a stent and balloon, preferably with structured mesh, using any of the tools and/or techniques described in the example embodiments discussed below. The modeled stent and balloon in their crimped state may be computationally positioned and bent in the 3D reconstructed vessel. In some embodiments, the stents and balloons are bent and positioned in the 3D reconstructed vessel following the true 3D course of the artery. Additionally, the computer can be configured to import design and material properties of the stents and balloons, generate a model of a stent and balloon, and/or position the modeled stent and balloon within or relative to the 3D reconstructed vessel lumen and surface of the vessel lumen using any of the tools and/or techniques described in the example embodiments discussed herein.

In some embodiments, the method repeats the IVUS/OCT/angiographic image acquisition and preparation for co-registration after PCI. An angiogram with the IVUS catheter in place is obtained, where automatic pullback (PB) of the catheter is performed. The system also marks IVUS PB start on angiography, through an automatic process. A quality check is run on the stents to ensure each is correctly placed; if adjustment is needed, this is done manually by the user.

Additionally, in some embodiments, an IVUS/OCT segmentation is repeated for the new images acquired after PCI. The automatic IVUS segmentation looks for underexpansion or malaposition of the stent as an additional quality check. Vessel morphometric and biomechanical measures are assessed based on the results of the check. A final quality check is run to ensure correct results. For example, the computer can be configured to assess morphometric measures including, but not limited to, stent expansion and apposition. The computer can be further configured to assess biomechanical measures (e.g., hemodynamic measures) including, but not limited to, fluid and solid stresses in the arterial lumen, wall and stent using computational fluid dynamics and finite element analysis. Additionally, the computer may be configured to assess stent and vessel morphometric and biomechanical measures based on computational method using any of the tools and/or techniques described in the example embodiments discussed herein.

The stiffness map, FFR map, and 3D visualization are automatically generated after the new 3D reconstruction is done.

The method can yield incremental information to the anatomical and functional assessment of coronary artery disease in the Cath Lab, guiding the percutaneous interventions. Patient-specific computational stenting models can reproduce controversial "what if" scenarios in a 3D environment in a cost- and time-effective fashion to elucidate the events occurring during the stenting procedure. These models characterize the local biomechanical microenvironment pre- and post-stenting, providing a framework for stenting optimization and generating new hypotheses that can then be tested clinically. In the era of powerful computers, predictive patient-specific computational simulations of bifurcation stenting are feasible and reliable.

Figure 3:
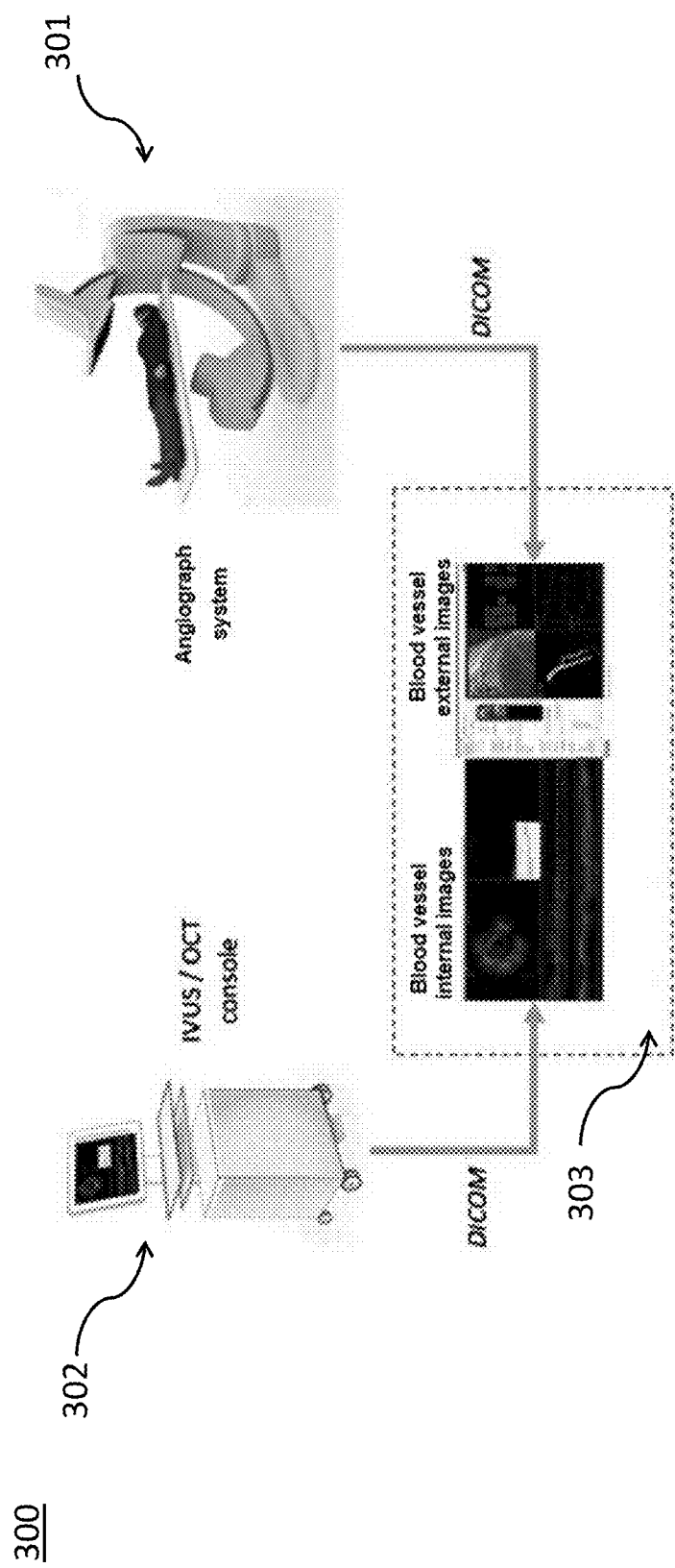
FIG. 3 illustrates the Angiography/IVUS/OCT imaging devices.
Figure 9:
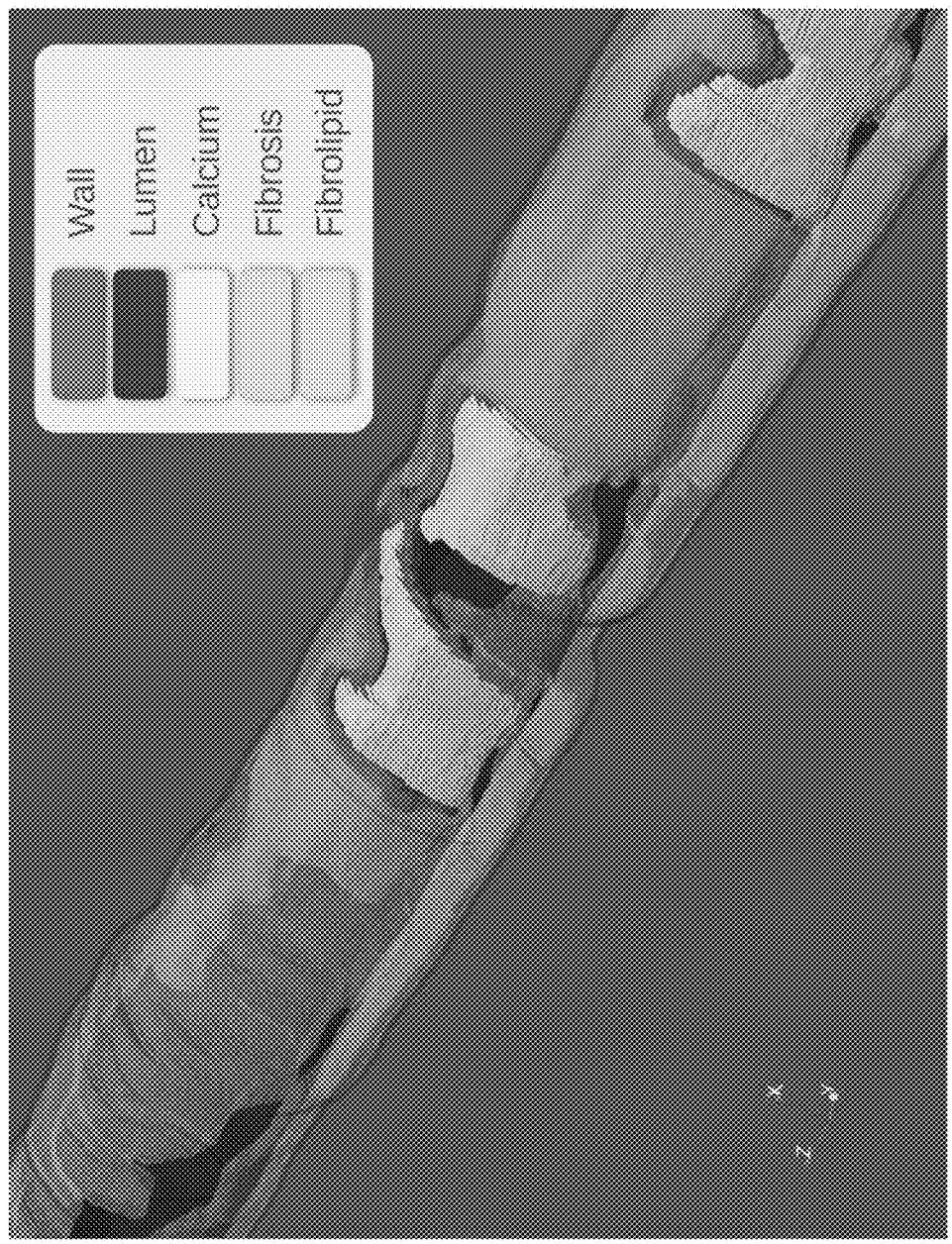
FIG. 9 is an exemplary visualization of AI-based IVUS image segmentation and reconstruction of a blood vessel, in accordance with one or more embodiments of the present disclosure.

FIG. 3 illustrates an implementable system 300 of the method that includes angiographic, IVUS and OCT imaging devices. The angiographic system 301 can capture the external images of the coronary artery of a patient and provide the images to the user and AI-based computer 303 for the 3D reconstruction. The IVUS and OCT devices 302 can provide the internal images of the coronary artery of a patient and provide the images to user and AI-based computer 303 for the image segmentations of lumen, wall, calcium, fibrous, fibro-lipid and the more intuitive 3D artery reconstruction. An exemplary segmentation and 3D reconstruction of IVUS imaging is shown in FIG. 9.

Figure 4:
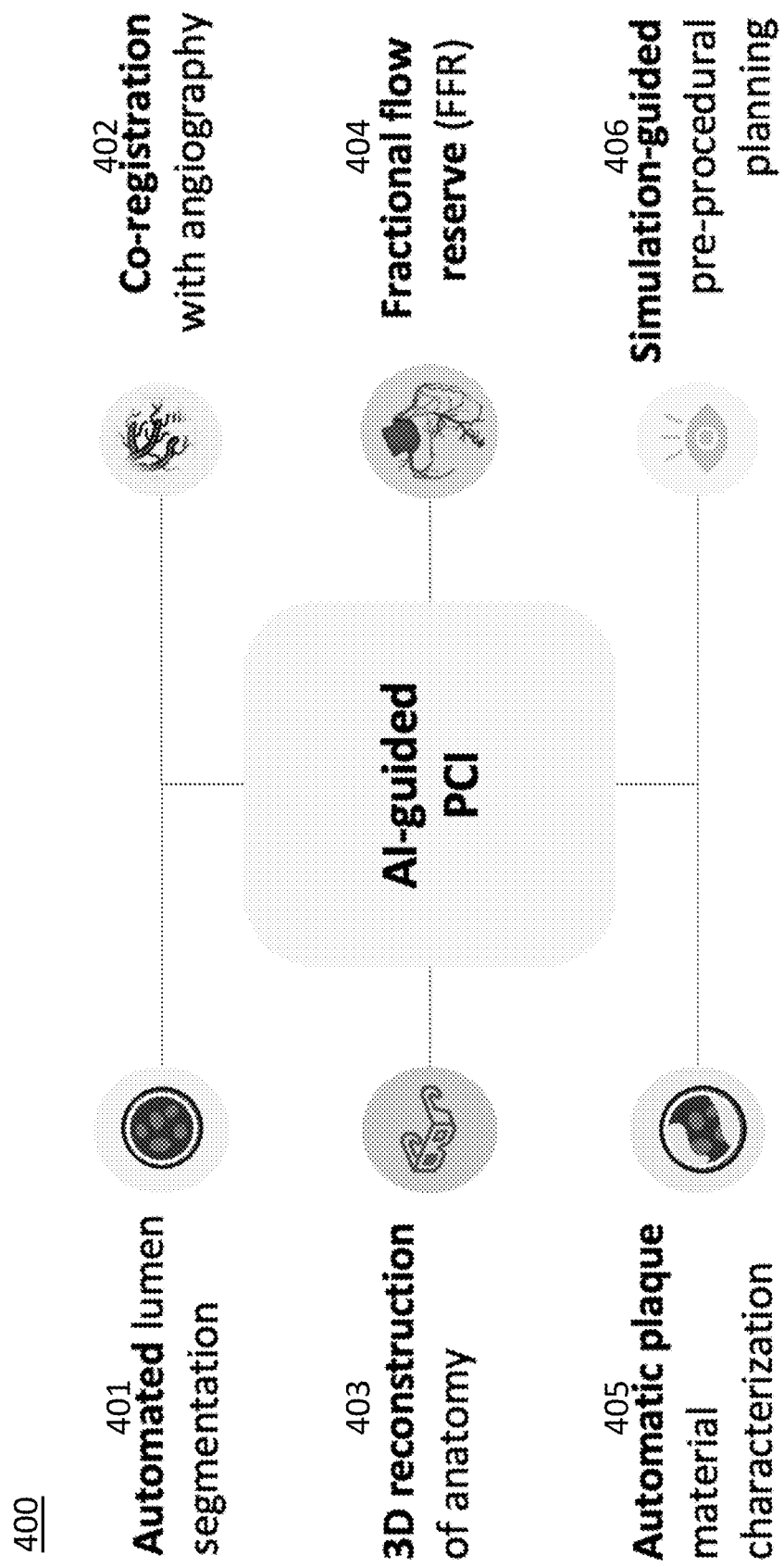
FIG. 4 is a schematic of an AI-guided PCI, in accordance with one or more embodiments of this disclosure.

FIG. 4 is a schematic 400 of an AI-guided PCI. The AI-guided PCI 400 may include one or more of the elements including an automated lumen segmentation 401, a co-registration with an angiography 402, a 3D reconstruction of anatomy 403, a FFR 404, an automatic plaque material characterization 405, and/or a simulation guided pre-procedural planning element 406.

Figure 5A:
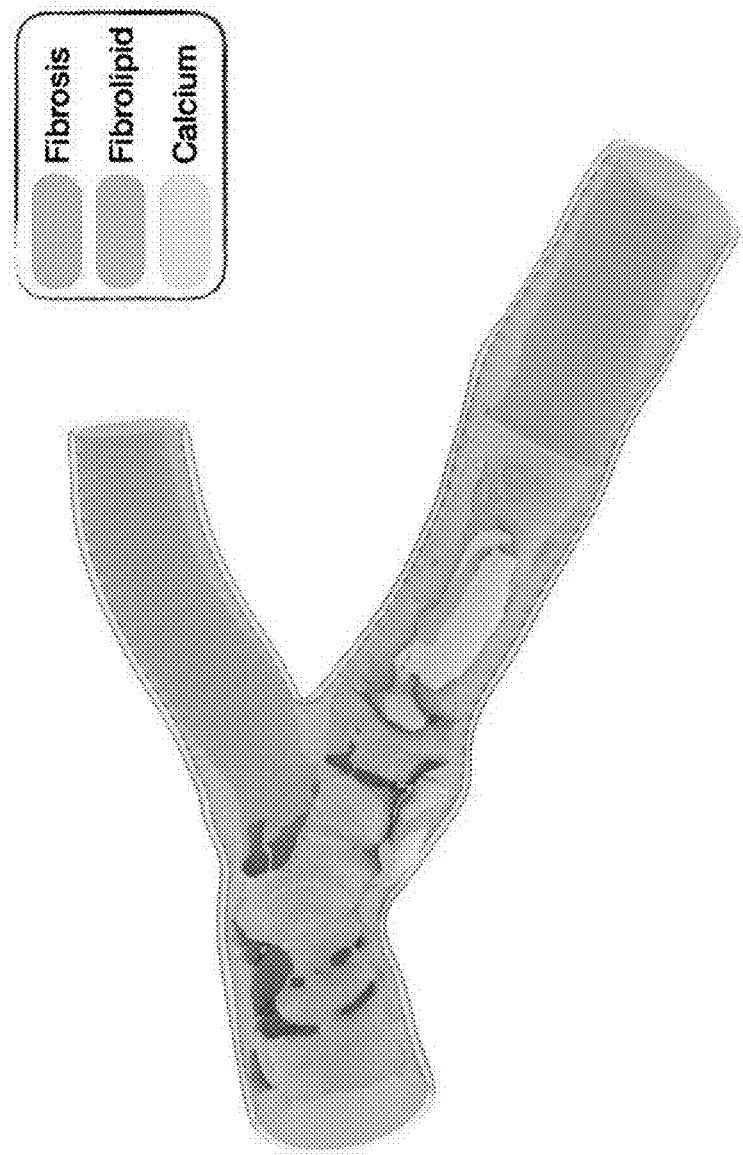
FIG. 5A illustrates an exemplary result of a material segmented vessel, in accordance with one or more embodiments of this disclosure.

FIG. 5A illustrates results of the material segmented vessel, in accordance with one or more embodiments of this disclosure. FIG. 5A is a pre-procedural 3D reconstructed vessel anatomy, showing a cross-section of a 3D reconstructed lumen, fibrosis, fibrolipid, and calcium. The 3D reconstructed model is more detailed and is used to represent the blood vessels with finite element analysis and solid mechanics for next level analysis.

Figure 5B:
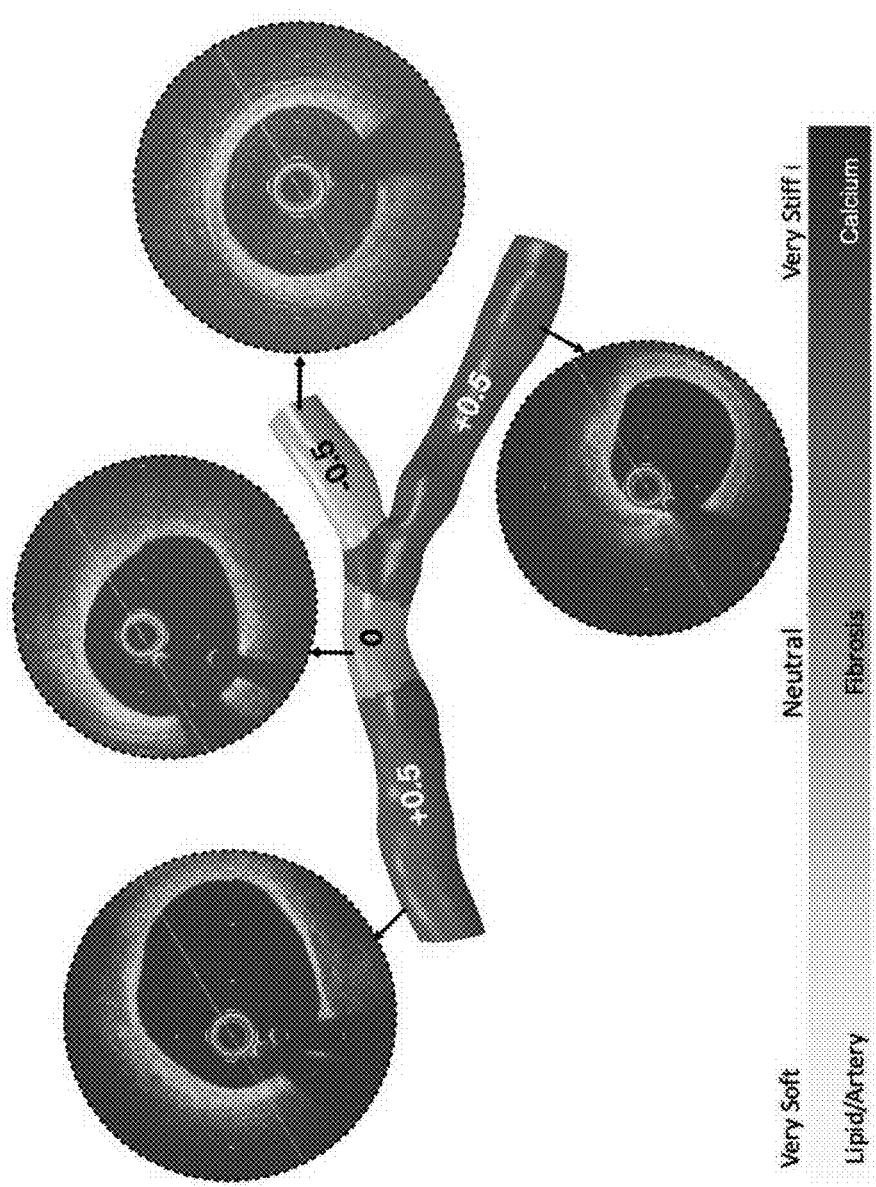
FIG. 5B illustrates an exemplary result of a vessel reflecting relative softness and stiffness, in accordance with one or more embodiments of this disclosure.

FIG. 5B is an example of an assignment of wall material properties, illustrating an exemplary result of a vessel reflecting relative softness and stiffness. In the computational simulation, this vessel cross-section was assigned +0.50 plaque stiffness based on OCT imaging.

FIG. 6 is an exemplary 3D reconstruction of a vessel from multiple angiographic projection images. The vessel image comprises branch labelling and root node detection, where the root node 601 is indicated in the image.

FIG. 7 illustrates automatic vessel lumen segmentation and reconstruction. The automated process beings with an AI-based segmentation of the vessel and its branche, before skeleton, boundary detection, and feature matching are automatically performed. Then a skeleton 3D reconstruction is automatically generated, and a lumen 3D reconstruction is output.

FIG. 8 is an exemplary visualization of AI-based IVUS image segmentation and reconstruction of a blood vessel. In the visualization process, an AI model is trained based on an angiogram and a ground truth. AI-based segmentation is automatically performed, as well as post-processing on the visualization. An overlay is automatically created for display over the vessel.

FIG. 9 is an exemplary segmented blood vessel, indicating where the vessel wall, lumen, calcium, fibrosis, and fibrolipid are located within the blood vessel.

Figure 10A:
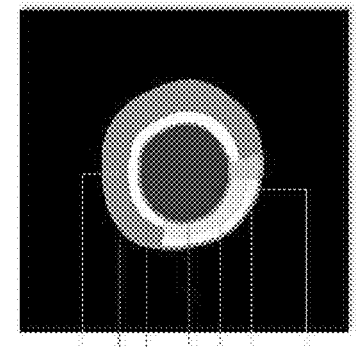
FIG. 10A is an exemplary visualization of a fully automatic IVUS plaque characterization, in accordance with one or more embodiments of this disclosure.
Figure 10A:
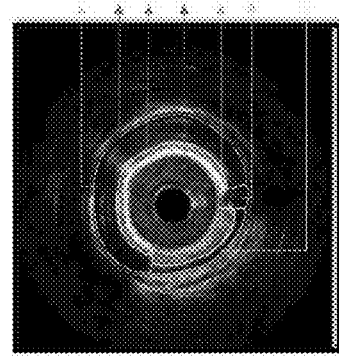
Figure 10A:
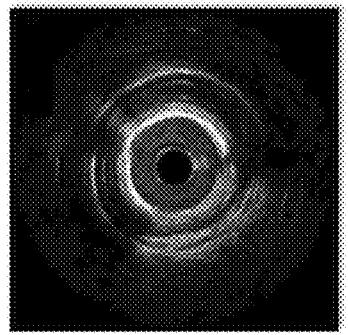

FIG. 10A illustrates a fully automatic IVUS plaque characterization, comprising a raw image 1201 and an AI prediction model image 1202 and visualization 1203.

Figure 10B:
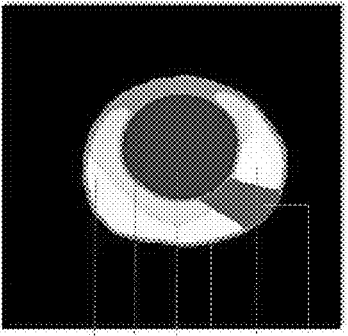
FIG. 10B is an exemplary visualization of a fully automatic OCT plaque characterization, in accordance with one or more embodiments of this disclosure.
Figure 10B:
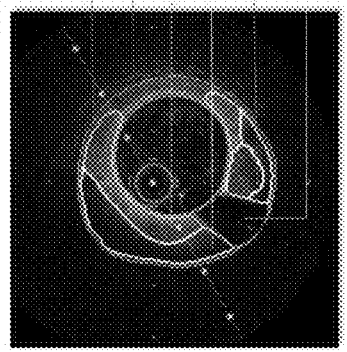
Figure 10B:
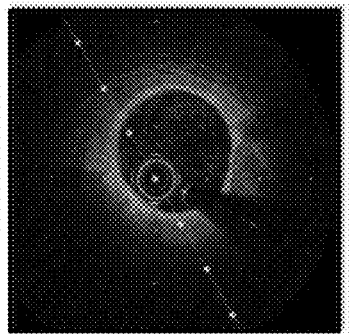

FIG. 10B illustrates a fully automatic OCT plaque characterization, comprising a raw image 1204 and an AI prediction model image 1205 and visualization 1206.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A method for providing automatic guidance of a percutaneous coronary intervention (PCI) procedure in real-time, comprising:
   receiving, at a computing node, a sequential plurality of images of a blood vessel of a subject from a catheter imaging system from at least a first and second view, the blood vessel having a lumen, a lumen surface, and a wall;
   providing the sequential plurality of images to a first neural network, the first neural network trained on a plurality of angiography images to output attention maps upon receiving input images;
   receiving, from the first neural network, an attention map for each of the sequential plurality of images;
   determining an average signal intensity for each attention map;
   determining a peak average signal intensity for each of the first and second views based on the average signal intensity for each attention map;
   selecting a first image of the sequential plurality of images having the first view that represents an end-diastolic cardiac phase based on the peak average signal intensity for the first view;
   selecting a second image of the sequential plurality of images having the second view that represents the end-diastolic cardiac phase based on the peak average signal intensity for the second view;
   identifying one or more landmark pairs in the first and the second images;
   building, at the computing node, a 3D model of the blood vessel based on the first image, the second image, and the one or more landmark pairs therebetween;
   segmenting, by a second neural network at the computing node, one or more materials between the lumen and the wall of the blood vessel appearing in the first image and the second image;
   reconstructing, at the computing node, the lumen surface based on the first and second image;
   determining, at the computing node, material properties of the blood vessel, the material properties including one or more of (a) a wall thickness, (b) a plaque thickness, (c) a lumen area, (d) a plaque eccentricity and (e) a plaque constituent;
   assigning, at the computing node, one or more material properties to the reconstructed lumen surface;
   generating, at the computing node, a recommendation to guide an interventional procedure in real-time based on the 3D reconstructed vessel lumen surface and segmented materials, the recommendation comprising at least a PCI plan;
   providing a display of an angiogram of the subject and the PCI plan superimposed upon the angiogram in real-time; and
   performing on the subject, using the 3D reconstructed vessel lumen surface and segmented materials:
   balloon catheter pre-dilation,
   a percutaneous coronary intervention catheter, and
   balloon catheter post-dilation.

2. The method of claim 1, wherein an imaging modality of the sequential plurality of images comprises one of a coronary angiography, intravascular ultrasound (IVUS), and/or optical coherence tomography (OCT).

3. The method of claim 1, wherein building a 3D model of the blood vessel comprises mapping a 2D vessel lumen image and a surface image to a 3D vessel centerline.

4. The method of claim 1, wherein performing the balloon catheter pre-dilation, the percutaneous coronary intervention catheter, and the balloon catheter post-dilation further comprises positioning and bending a modeled stent and balloon in a crimped state in the 3D reconstructed vessel lumen, wherein the 3D model is computationally based on a 2D imaging plane.

5. The method of claim 1, wherein the second neural network model is a deep neural network, convolutional neural network, a U-NET network, and/or a machine learning model.

6. The method of claim 1, wherein performing balloon pre-dilation catheter, PCI catheter, and balloon catheter post-dilation comprises computing a position for a device using finite element analysis.

7. The method of claim 1, further comprising:
associating one or more material properties with the one or more segmented materials; and
assigning a plaque stiffness to the blood vessel based on the one or more segmented materials.

8. The method of claim 1, further comprising:
calculating a fractional flow reserve for a plurality of locations within the lumen of the blood vessel; and
displaying a fractional flow reserve map on the 3D model.

9. The method of claim 1, wherein the sequential plurality of images comprise data from a coronary angiography, an intravascular ultrasound, or an optical coherence tomography.

10. The method of claim 1, further comprising:
determining a centerline of the reconstructed vessel lumen surface receiving one or more blood vessel sectional images; and
attaching the sectional images to the centerline of the reconstructed vessel lumen surface.

11. The method of claim 10, further comprising:
measuring a set of parameters from the reconstructed vessel lumen surface;
determining a series of solid and fluid mechanical values based on the measured parameters and computational simulations; and
providing additional guidance for the interventional procedure based on the solid and fluid mechanical values.

12. The method of claim 10, wherein the 3D model is reconstructed a second time with the attached sectional images and 3D centerlines of the blood vessel on a 2D imaging plane.

13. The method of claim 1, wherein the blood vessel is a coronary artery.

14. The method of claim 1, wherein guiding the interventional procedure in real-time is based on AI-based 3D reconstructed data.

15. The method of claim 1, further comprising:
performing a fractional flow reserve calculation;
generating, based on the fractional flow reserve calculation, a fractional flow reserve map; and
displaying the fractional flow reserve map along the blood vessel.

16. The method of claim 15, further comprising determining a risk for a location along the blood vessel based on the fractional flow reserve map.

17. The method of claim 15, wherein performing a fractional flow reserve calculation comprises:
determining a differential between a mean aortic pressure and a mean distal pressure within the blood vessel; and
dividing the mean distal pressure by the mean aortic pressure.

18. The method of claim 1, further comprising automatically generating a stiffness map of the blood vessel, and wherein generating the stiffness map comprising determining a stiffness of a plurality of locations along the blood vessel.

19. The method of claim 18, wherein a recommendation for a pre-dilation technique is automatically generated based on the stiffness map.

20. The method of claim 1, further comprising outputting a recommendation for a diagnosis of severity of coronary artery disease.

21. The method of claim 1, further comprising outputting the PCI planning decision.

22. The method of claim 21, wherein the PCI planning decision comprises a recommended stent size.

23. The method of claim 1, further comprising outputting a recommendation for a percutaneous coronary intervention optimization parameter.

24. The method of claim 1, further comprising:
selecting the best image of the sequential plurality of images;
automatically recognizing in real-time the phase of the cardiac cycle based on time-frequency analysis of motion patterns of the blood vessel; and
automatically recognizing in real-time the level of contrast flow in the image.

25. The method of claim 1, wherein the selection of the best image comprises automatic identification in real-time of a high-contrast end-diastolic image using time-frequency analysis of motion patterns of the blood vessel.

26. The method of claim 1, further comprising:
dividing, at the computing node, the 3D model of the blood vessel into a plurality of zones;
wherein assigning the one or more material properties to the reconstructed lumen surface further comprising one or more material properties to each zone of the plurality of zones.

27. The computer program product of claim 26, wherein guiding the interventional procedure comprises providing a clinical decision support system (CDSS).

* * * * *